(12) United States Patent
Chefitz et al.

(10) Patent No.: US 12,121,321 B2
(45) Date of Patent: *Oct. 22, 2024

(54) SELF-ADMINISTERED, NON-INVASIVE, TRANSCUTANEOUS VIRAL DETECTOR

(71) Applicant: 123IV, Inc., New Rochelle, NY (US)

(72) Inventors: Allen B. Chefitz, New Rochelle, NY (US); Rohit Singh, Newton, MA (US)

(73) Assignee: 123IV, Inc., New Rochelle, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/954,026

(22) Filed: Sep. 27, 2022

(65) Prior Publication Data
US 2023/0015076 A1 Jan. 19, 2023

Related U.S. Application Data

(60) Continuation of application No. 17/722,681, filed on Apr. 18, 2022, now Pat. No. 11,452,454, and a division of application No. 17/079,649, filed on Oct. 26, 2020, now Pat. No. 11,304,605.

(60) Provisional application No. 63/053,806, filed on Jul. 20, 2020.

(51) Int. Cl.
*A61B 5/00* (2006.01)

(52) U.S. Cl.
CPC .......... *A61B 5/0075* (2013.01); *A61B 5/6826* (2013.01); *A61B 5/6888* (2013.01); *A61B 5/7264* (2013.01); *A61B 5/7282* (2013.01); *A61B 5/7405* (2013.01); *A61B 5/742* (2013.01); *A61B 5/7455* (2013.01); *A61B 2562/0238* (2013.01); *A61B 2562/0285* (2013.01)

(58) Field of Classification Search
CPC .... A61B 2562/0238; A61B 2562/0285; A61B 5/0075; A61B 5/6826; A61B 5/6888; A61B 5/7264; A61B 5/7282; A61B 5/7405; A61B 5/742; A61B 5/7455
See application file for complete search history.

(56) References Cited

U.S. PATENT DOCUMENTS

| 11,304,605 | B2 * | 4/2022 | Chefitz | A61B 5/7282 |
| 11,452,454 | B2 * | 9/2022 | Chefitz | A61B 5/7264 |

(Continued)

*Primary Examiner* — Michael T Rozanski
(74) *Attorney, Agent, or Firm* — David H. Judson

(57) ABSTRACT

A non-invasive, transcutaneous, real-time viral detection device that is configured for self-administration, e.g., at a user's home. In one embodiment, and after positioning the device relative to the human body part (e.g., the user's finger), light sources in the device are activated (excited), and resulting data captured. In particular, a set of Raman spectra are collected from a configured set of emitters and detectors in the device and delivered to a nearby receiver, preferably wirelessly. The receiver filters and de-convolves the Raman spectra producing a data set representative of the constituent elements in the user's tissue of interest. The data set is applied against a statistical classifier, e.g., a neural network that has been trained to recognize and distinguish the absence or presence of viral components, e.g., C-19, or its associated blood-borne acute phase reactants. The classifier outputs an appropriate indicator, preferably in real-time, providing the user with an immediate indication of whether C-19 (or other virus of interest) is present.

3 Claims, 2 Drawing Sheets

(56) References Cited

U.S. PATENT DOCUMENTS

2016/0177366 A1\* 6/2016 Auner .................. G01J 3/2823
  435/5
2016/0334332 A1\* 11/2016 Magnussen ........ A61B 5/14546

\* cited by examiner

SELF-ADMINISTERED, NON-INVASIVE, TRANSCUTANEOUS VIRAL DETECTOR

This application is a continuation of U.S. Ser. No. 17/722, 681, filed Apr. 18, 2022, now U.S. Pat. No. 11,452,454, which application was a division of U.S. Ser. No. 17/079, 649, filed Oct. 26, 2020, now U.S. Pat. No. 11,304,605, which application was based on and claimed priority to U.S. Ser. No. 63/053,806, filed Jul. 20, 2020.

BACKGROUND

Technical Field

The subject matter herein relates to diagnostic devices configured for self-administered, non-invasive, transcutaneous, real-time detection of virus, such as SARS-CoV-2 virus, and influenza virus.

Brief Description of the Related Art

Covid-19 (C-19) is a positive single-stranded RNA genome that contains 29891 nucleotides, encoding for 9860 amino acids. The genome is 30 kb in length, the largest of many viruses. Targets for identification include the virus structure, proteins and antibodies. A definitive Covid-19 infection typically is diagnosed by laboratory tests, including real-time Polymerase Chain Reaction (PCR)-based testing, and serological testing is now also available for detecting SARS-CoV-2 antibodies in a patient's blood. These currently available approaches require the patient to provide a body fluid specimen. Other described proposals for contact tracing and even diagnosis (e.g., network-based phone tracing) do not provide personal diagnosis, let alone in real-time, or near real-time.

Recently, Jacobi et al have proposed the uses of low-frequency Surface Enhanced Raman Spectroscopy (SERS) as a diagnostic tool for C-19 and other coronaviruses. They suggest that samples may be taken non-invasively by illuminating the patient's body with a laser directed at the lungs, or naval cavity, etc., and then collecting spectra that should be present in cases of viral infection. In an experimental optical detection setup (not based on a human subject), the authors describe a reflection geometry that consists of an excitation laser at wavelength $\lambda_{exc}$=532 nm, which is focused on an analyte using a microscope objective lens, which also collects the Raman-scattered light. In this example setup, the collection geometry is decoupled from the excitation geometry using a beam splitter. The decoupled Raman signal is filtered to block the laser excitation from passing into the detector. The signal beam is coupled to an imaging spectrometer, where an optical grating resolves the spectrum and projects it onto a charge-coupled device (CCD).

Handheld Raman spectrometers are known and used for signal acquisition. An example is the Raman Explorer 785 device, available from Headwall Photonics. This spectrometer can be miniaturized to fit within a pad applied to the finger or wrist. It has also been proposed for use in Spatially Offset Raman Spectroscopy (SORS) to distinguish molecules beneath the surface of the skin. In an example setup, and for sample excitation, light from a 785-nm laser module is delivered by optical fiber and focused onto the sample surface, e.g., the finger, wrist or earlobe, at a fixed 45° incident angle by a laser focus unit. In this approach, both the sample and the laser focus units are fixed on a motorized positioning platform for synchronized movement, and so as to maintain a fixed excitation spot on the sample surface for collection of Raman spectral signals at different offset distances using a fixed-position Raman probe. The spectral data acquisition and movement of the motorized platform are software-controlled. The system acquires initial spectra at no offset, and then moves the sample and laser focus unit, incrementally increasing the offset, and continuing the spectra capture (using the fixed-position Raman probe) at each spatial offset. A large number of spectra are collected, and then a multivariate analysis is applied to detect presence or absence of the virus.

While the above-describe Raman spectra-based detection approaches suggested by these authors holds promise for early and non-invasive coronavirus infection, there remains a need to provide a practical, cost-effective, highly-accurate testing device that provides real-time (immediate) results.

BRIEF SUMMARY

This disclosure provides for non-invasive, transcutaneous, real-time viral detection device that is configured for self-administration, e.g., at a user's home. After positioning the device relative to the human body part (e.g., the user's finger), light sources in the device (e.g., LEDs) are activated (excited), and resulting data captured by a set of associated detectors (e.g., CCDs). To this end, a plurality of emitter-detector pairs (i.e., one LED and its associated detector) are arranged, preferably with multiple ones of the emitters configured closely adjacent to one another and configured to be concurrently activated. As the emitters are excited, the associated detectors capture information for each emitter-detector pair. The information corresponds to a given area or region (or point) in a blood vessel, and that may or may not include (at that location) viral particles of interest, such as SARS-CoV-2, or other blood-borne abnormalities associated with Covid-19. The information, which represents a degree of light absorption at the location, constitutes a Raman spectra, and it is collected for each of co-excited emitter-detector pairs. This collection of information is delivered to a nearby receiver, preferably wirelessly. The receiver filters and de-convolves the Raman spectra producing a data set representative of the structure in the user's blood vessel. The data set is applied against a statistical classifier, that has been previously trained to recognize patients who have been found to test positive for disease such as Covid-19, and patients who have been found to test negative for that disease. The classifier outputs an appropriate indicator, preferably in real-time, providing the user with an immediate indication of whether SARS-CoV-2 (or other virus) is present. The foregoing has outlined some of the more pertinent features of the subject matter. These features should be construed to be merely illustrative. Many other beneficial results can be attained by applying the disclosed subject matter in a different manner or by modifying the subject matter as will be described.

BRIEF DESCRIPTION OF THE DRAWINGS

For a more complete understanding of the subject matter and the advantages thereof, reference is now made to the following descriptions taken in conjunction with the accompanying drawings, in which.

DETAILED DESCRIPTION

Figure 1:
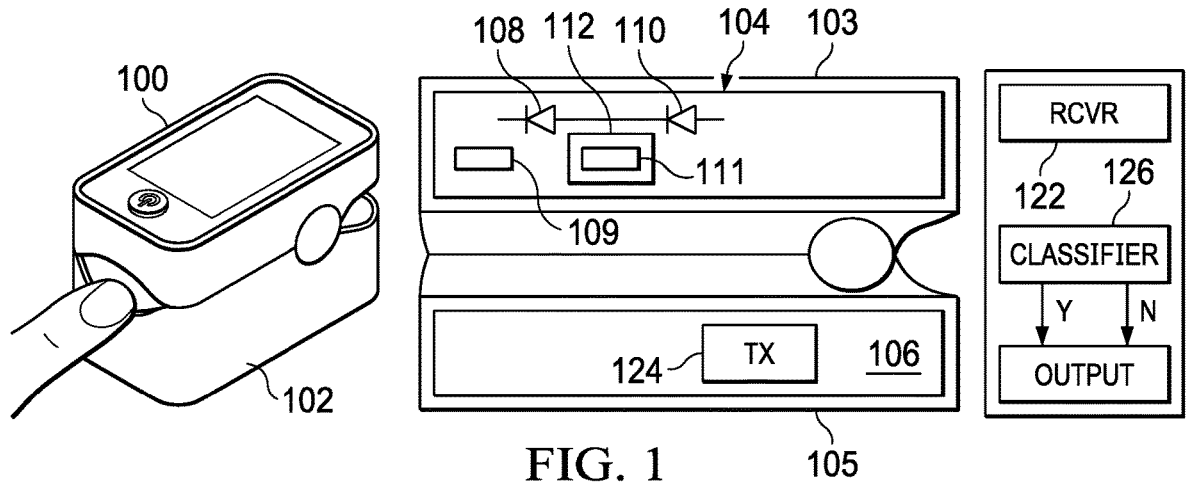
FIG. 1 is a diagram depicting a representative detection device according to a first embodiment of this disclosure.

In one embodiment, and with reference to FIG. 1, a device 100 comprises a housing 102 that supports a pair of pads, namely, a first (upper) portion 103 comprising a silica pad 104, and an opposed second (lower) portion 105 comprising a silica pad 106. The pads are optional. The housing 102 supports the first and second portions in opposed relation to one another, and in this embodiment the housing is configured to be positioned around a patient's tissue of interest, e.g., a fingertip, at which the viral measurement is being carried out. The positioning itself is not critical as long as the device is positioned relative to the vascularized tissue of interest, and in this embodiment the device is configured to be self-positioned. As depicted, the device 100 comprises a number of light sources. In a preferred embodiment, pad 104 supports emitters (e.g., LEDs) 108 and 110 that are positioned closely adjacent one another and configured to be excited at a first wavelength, e.g., 785 nm. Other excitation wavelengths, e.g., 532 nm, may be used. Each emitter has an associated detector (e.g., a Charge Coupled Device (CCD) 109 and 111. Therefore, emitter 108 and detector 109 comprise a first emitter-detector pair, and emitter 110 and detector 111 comprise a second emitter-detector pair. As depicted, the emitters 108 and 110 are located side-by-side and separated by a spacing that is as small as possible given the physical constraints so that when the LEDs are excited concurrently, their associated CCD detectors capture reflections (scattered light) along two different lines of sight that spaced as close as possible with respect to the tissue.

The first and second emitter-detector pairs are a minimum configuration, and preferably there are many more emitter pairs (each comprising an emitter and an associated detector) configured in the first portion. One or more of the emitters in these additional emitter-detector pairs may be configured at an angle (e.g., 45°) relative to the other emitters, e.g., in the first and second emitter pairs. Preferably, there are also additional emitter-detector pairs located in the opposed pad. The number of emitter-detector pairs thus may vary, as may their locations and relative positioning to one another. In addition, at least some of the detectors in the emitter-detector pairs are coated with a conductive material 112, e.g., silver or gold nanoparticles. It is not required that all detectors have this type of conductive coating, and typically some of the detectors are uncoated. Some of the emitters in the emitter-detector pairs may be configured to illuminate at one wavelength (e.g., 785 nm) while other emitters in the emitter-detector pairs are configured to illuminate at a second wavelength (e.g., 532 nm). These wavelengths are not intended to be limiting, and two or more different wavelengths may be used.

Preferably, the emitters in the pairs are configured to be synchronized such that all of the emitters are illuminated concurrently or as near concurrently as possible. This illumination serves to bath the tissue of interest with a relatively large number of point sources that are trained on the tissue of interest, in this example a blood vessel that may or may not be carrying viral particles of interest. The detectors in the emitter-detector pairs capture light scattered by whatever particles may be present in the tissue. In particular, and as the emitters are excited, the associated detectors capture information for each emitter-detector pair. The information corresponds to a given area or region (or point) in a blood vessel, and that may or may not include (at that location) viral particles of interest, such as SARS-CoV-2, or associated acute phase reactants not limited to cytokines, interferons, procalcitonin, C-reactive protein, serum amyloid A, hepcidin, haptoglobin, ferritin, alpha-1-antitrypsin, transferrin, albumin, interleukins, or other plasma reactants whose concentrations increase or decrease in association with Covid-19, and other patterns unique to Covid-19. The information, which represents a degree of light absorption at the location, constitutes a Raman spectra, and it is collected for each of co-excited emitter-detector pairs. In this embodiment, this collection of information is delivered to a nearby receiver 122, preferably wirelessly, by transmitter 124. The receiver 122 filters and de-convolves the Raman spectra producing a data set representative of the structure in the user's blood vessel. The data set is applied against a statistical classifier 126 that has been previously trained to recognize patients who have been found to test positive for disease such as Covid-19, and patients who have been found to test negative for that disease. The classifier 126 outputs an appropriate indicator, preferably in real-time, providing the user with an immediate indication of whether SARS-CoV-2 (or other virus) is present.

Typically, transmitter 124 is Bluetooth-based. Generalizing, signals captured by the detector are wirelessly transmitted to an associated detector system (e.g., a computing device) for real-time analysis and notification regarding the presence of absence of the virus, e.g., taking into consideration its unique associated reactants. The configuration of the detector system may vary but typically includes a receiver component (to receive the signals output from the detector, processing components, and associated input/output devices). In one embodiment, the detector system is a computer having a receiver to receive the signals generated by the detector. The computer executes an application that processes the received signals and generates an output indication. Preferably, a SORS-based detection algorithm is used for this purpose. Depending on the distance between the detector-embedded transmitter and the associated receiving device, other over-the-air (OTA) signal transport mechanisms may be used (e.g., WiFi). There is no requirement that a particular type of wireless transport be used, and in an alternative embodiment the device itself may be coupled to the signal processing components in a wired manner.

In this embodiment, the housing is self-positioned about the user's body part, e.g., the finger, and the LEDs activated simultaneously (or near-simultaneously). The above-described physical arrangement of the emitter-detector pairs introduces spectral shifts in a relatively large size of data (the captured spectra) to enable the real-time SORS-based detection. The multiple light sources positioned from the multiple angular perspectives are excited, with the resulting spectra (individual snapshots) captured and transmitted to the receiver for analysis. Preferably, these multiple snapshots are captured simultaneously (or as near simultaneous as possible). At the receiver, the individual snapshots are filtered (if necessary) and passed through a deconvolution process. The resulting output is then applied as an input to a statistical model, which preferably outputs one of two labels: a first label indicating presence of virus, and a second label indicating absence of virus. An indeterminate response may also be provided if, for example, the detected signaling is insufficient to enable a definitive determination to be made; when an indeterminate response occurs, an indication to this effect may be provided to the user, e.g., to re-position the device and redo the test.

The output may be provided visually, aurally, in a tactile manner (e.g., with haptic technology that effects a vibration, a movement, a force, etc.), by signaling another device (e.g., a mobile device, a smart watch, etc.) that in turn provides the notification, or in any other convenient manner.

Figure 2:
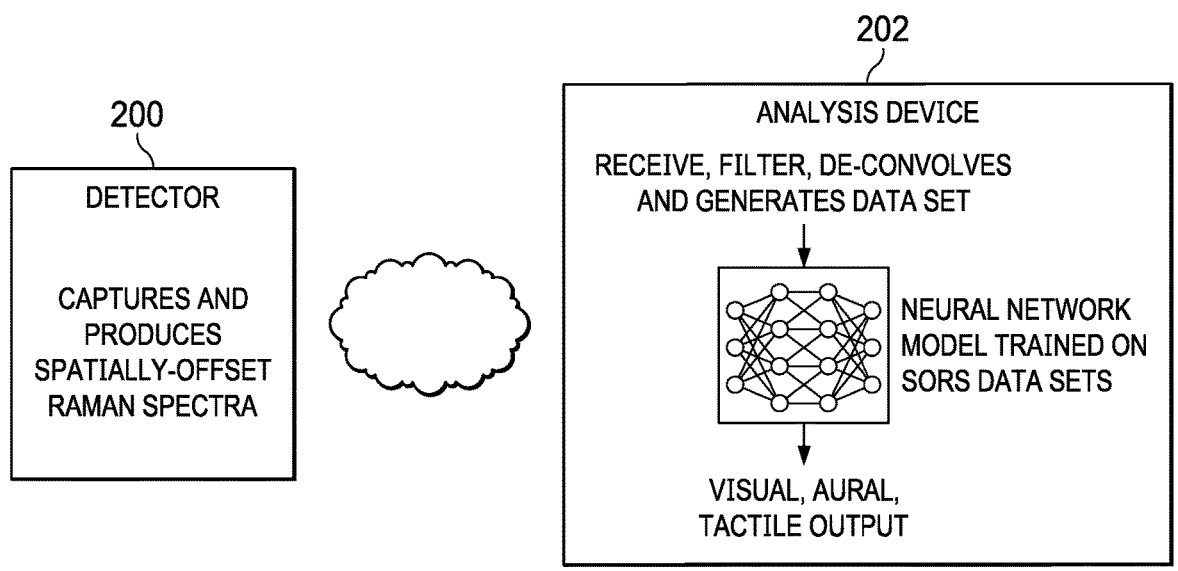
FIG. 2 is a block diagram of a detection system that incorporates the detection device shown in FIG. 1.

FIG. 2 depicts a representative system that comprises the detector device 200, and an associated analysis device 202. The detector captures and produces the spatially-offset Raman spectra, and transmits those signals to the analysis device, typically wirelessly. The analysis device filters the received signals, provides de-convolution, and generate a data set for analysis. The data set is then passed through a statistical classifier that has been trained (from other human patients) to analyze signals captured in this manner. The classifier outputs an indication of the presence or absence of the viral constituents of interest (e.g., coronavirus, influenza, etc.) The analysis device then outputs the result, preferably visually, aurally, by tactile indication, or otherwise. In this embodiment, the detector and analysis components are distinct (and coupled via the communication medium such as the wireless link), but this is not a requirement. In an alternative embodiment, the signal processing components are co-located in the detector device housing itself, such that transmission of the captured signals is not required. In this embodiment, the device housing also includes a visual, audible or tactile indicator of the signal analysis.

Preferably, the statistical model used for viral constituent discrimination is a neural network, such as a convolutional neural network (CNN) classifier that has been trained against training data captured from other patients, at least some of which have the virus. The nature and type of Machine Learning (ML) algorithms that are used to process the patient-captured data (from other patients) into one or more data models may vary. The ML algorithms iteratively learn from the patient-captured data, thus allowing the system to find hidden insights without being explicitly programmed where to look. ML tasks are typically classified into various categories depending on the nature of the learning signal or feedback available to a learning system, namely supervised learning, unsupervised learning, and reinforcement learning. In supervised learning, the algorithm trains on labeled historic data and learns general rules that map input to output/target. The discovery of relationships between the input variables and the label/target variable in supervised learning is done with a training set, and the system learns from the training data. In this approach, a test set is used to evaluate whether the discovered relationships hold and the strength and utility of the predictive relationship is assessed by feeding the model with the input variables of the test data and comparing the label predicted by the model with the actual label of the data. The most widely used supervised learning algorithms are Support Vector Machines, Linear Regression, Logistic Regression, Naive Bayes, and Neural Networks.

In unsupervised machine learning, the algorithm trains on unlabeled data. The goal of these algorithms is to explore the data and find some structure within. The most widely used unsupervised learning algorithms are Cluster Analysis and Market Basket Analysis. In reinforcement learning, the algorithm learns through a feedback system. The algorithm takes actions and receives feedback about the appropriateness of its actions and based on the feedback, modifies the strategy and takes further actions that would maximize the expected reward over a given amount of time.

The following provides additional details regarding supervised machine learning, which is the preferred technique used in the learning approach herein. As noted above, supervised learning is the machine learning task of inferring a function from labeled training data. The training data consist of a set of training examples. In supervised learning, typically each example is a pair consisting of an input object (typically a vector), and a desired output value (also called the supervisory signal). A supervised learning algorithm analyzes the training data and produces an inferred function, which can be used for mapping new examples. An optimal scenario allows for the algorithm to correctly determine the class labels for unseen instances. This requires the learning algorithm to generalize reasonably from the training data to unseen situations.

For supervised learning, the following steps are used. An initial determination is what kind of data is to be used as a training set. Here, the training data preferably are Raman spectra captured from other patients using the device configuration described above. The training set is then gathered. In particular, during the training phase, and for each laser source and receiver combination, the absorption spectrum is measured, quantized, and digitized. An input feature vector for each patient (in the training data set) preferably comprises of such measurements from each source and receiver pair, along with corresponding information about the positioning and orientation of the pair, any metallic coatings and laser wavelength etc.

Generalizing, a set of input objects is gathered and corresponding outputs are also gathered from measurements using the described device. Then, an input feature representation of the learned function is determined. In this approach, the input object is transformed into a feature vector, which contains a number of features that are descriptive of the object. The structure of the learned function and corresponding learning algorithm are then determined. For example, support vector machines or decision trees may be used. The learning algorithm is then run on the gathered training set. Some supervised learning algorithms require a user to determine certain control parameters. These parameters may be adjusted by optimizing performance on a subset (called a validation set) of the training set, or via cross-validation. The accuracy of the learned function is then evaluated. After parameter adjustment and learning, the performance of the resulting function is measured on a test set that is separate from the training set. The result of this training process is the machine learning classifier that is then instantiated in the receiver of the system.

As described above, the receiving and processing components are supported in a separate housing, such as in an associated computer. This is not a requirement. In an alternative embodiment, the receiver associated with the detector is supported in a mobile device, such as a smartphone, tablet, or wearable computing device. Such a device comprises a CPU (central processing unit), computer memory, such as RAM, and a drive. The device software includes an operating system (e.g., Google® Android™, or the like), and generic support applications and utilities. The device may also include a graphics processing unit (GPU).

Generalizing, the mobile device that provides the receiving and signal processing functionality is any wireless client device, e.g., a cellphone, pager, a personal digital assistant (PDA, e.g., with GPRS NIC), a mobile computer with a smartphone client, or the like. Other mobile devices in which the technique may be practiced include any access protocol-enabled device (e.g., an Android™-based device, or the like) that is capable of sending and receiving data in a wireless manner using a wireless protocol. Typical wireless protocols are: WiFi, GSM/GPRS, CDMA or WiMax. These protocols implement the ISO/OSI Physical and Data Link layers (Layers 1 & 2) upon which a traditional networking stack is built, complete with IP, TCP, SSL/TLS and HTTP.

As noted, there is no limitation on the underlying network transport that may be used between the detector and the receiver. This may be any communication medium including, without limitation, cellular, wireless, Wi-Fi, Bluetooth, small cell (e.g., femto), and combinations thereof.

The receiver implements one or more of the above-described processes (filtering, deconvolution, applying the statistical model, and providing the output indication (or signaling) preferably using one or more processes. Each above-described process preferably is implemented in computer software as a set of program instructions executable in one or more processors, as a special-purpose machine. Representative machines on which the subject matter herein is provided may be hardware running a Linux or Linux-variant operating system and one or more applications to carry out the described functionality.

While the disclosed subject matter has been described in the context of a method or process, the subject matter also relates to apparatus for performing the operations herein. This apparatus may be a particular machine that is specially constructed for the required purposes, or it may comprise a computer otherwise selectively activated or reconfigured by a computer program stored in the computer. Such a computer program may be stored in a computer readable storage medium, such as, but is not limited to, any type of disk including an optical disk, a CD-ROM, and a magnetic-optical disk, a read-only memory (ROM), a random access memory (RAM), a magnetic or optical card, or any type of media suitable for storing electronic instructions, and each coupled to a computer system bus.

A given implementation of the computing platform is software that executes on a hardware platform running an operating system. A machine implementing the techniques herein comprises a hardware processor, and non-transitory computer memory holding computer program instructions that are executed by the processor to perform the above-described methods.

Any computing entity (system, machine, device, program, process, utility, or the like) may act as the receiving component. The receiving and signal processing functionality may be co-located or various parts/components may be separately and run as distinct functions, perhaps in one or more locations (over a distributed network).

The techniques herein generally provide for the above-described improvements to a technology or technical field, as well as the specific technological improvements to various fields, all as described above.

Figure 3:
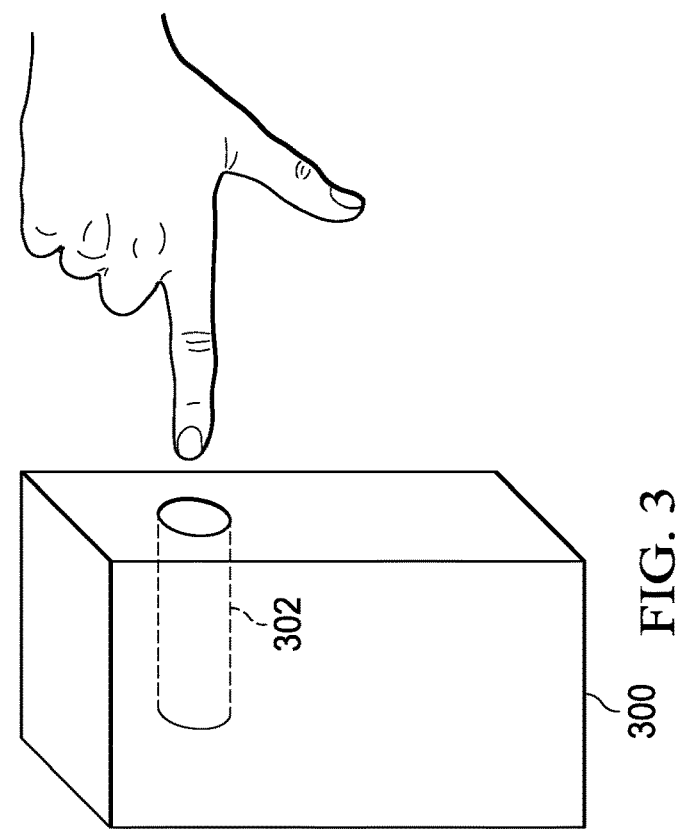
FIG. 3 depicts another portable detector that incorporates the techniques of this disclosure.

FIG. 3 depicts a first alternative embodiment wherein all components are self-contained within a housing 300 that includes a finger-receiving tube 302. In this embodiment, the user places his or her finger in the tube 302, the emitter-detector pairs such as described above are illuminated, the resulting images captured (the Raman spectra) and analyzed by the classifier, and the result is output to the user directly. In a variant embodiment, the tube 302 is a rotating cylindrical tube into which the user inserts a finger or other vascularized body part. As described above, optical elements in the housing 300 are excited, e.g., at 785 nm, 532 nm, or the like, near simultaneously. A Raman probe within the housing then captures the scattered light and provides/transmits it to the CCD detectors (coated and uncoated). Spectral analysis is then performed and a result immediately displayed or otherwise output.

Figure 4:
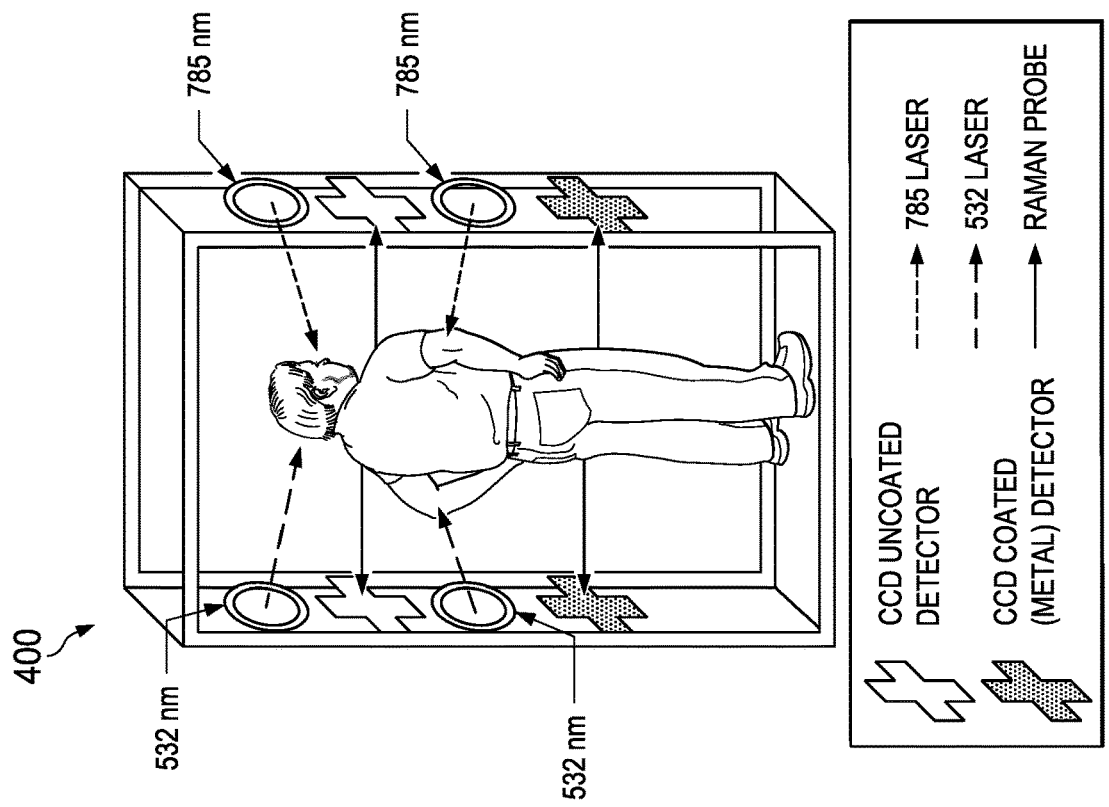
FIG. 4 depicts a full body scanner that incorporates the operating principles of this disclosure in another embodiment.

FIG. 4 depicts a second alternative embodiment that is a full body scanner 400. The user walks into the scanner and is positioned for the scan. The emitter-detector pairs such as described are illuminated, the resulting images captured and analyzed, and once again the result is output directly (either to the user or to another person).

What is claimed is as follows:

1. An apparatus, comprising:
    a housing comprising a base, and an upstanding portion, the upstanding portion supporting a tube configured to receive a finger of a human hand;
    a laser source;
    a detection system supported in the housing and comprising electronics configured in response to receipt of the finger in the tube to activate the laser source, thereby illuminating a portion of the finger received in the tube, and to capture a spatially-offset Raman spectra from blood-borne constituents, the capture being non-invasive and transcutaneous, wherein there is a degree of spatial offset in the Raman spectra;
    the detection system further including program code executed by a processor and configured to (i) process the Raman spectra into a data set, (ii) apply the data set to a binary classifier that has been previously trained from a set of learning examples using a support vector machine (SVM) or a decision tree algorithm to distinguish data sets representing either presence or absence of given particles of interest in the blood-borne constituents; and (iii) generate a signal indicating the presence or absence of the given particles of interest; and
    an output device that receives the signal and in real-time outputs an indication that the given particles of interest have been identified.

2. The apparatus as described in claim 1 wherein the particles of interest comprise one of: cytokines, interferons, procalcitonin, C-reactive protein, serum amyloid A, hepcidin, haptoglobin, ferritin, alpha-1-antitrypsin, transferrin, albumin, interleukins, and other plasma reactants whose concentrations increase or decrease in association with presence of SARS-CoV-2.

3. The apparatus as described in claim 1 wherein the indication is one of: a visual indicator, an aural indicator, and a tactile indicator.

* * * * *